US005760267A

United States Patent [19]
Gandolfi et al.

[11] Patent Number: 5,760,267
[45] Date of Patent: Jun. 2, 1998

[54] PROCESS FOR PREPARING 1-(3-TRIALKYLSILYLPHENYL)-2,2,2-TRIFLUOROMETHYL ETHANONE DERIVATIVES

[75] Inventors: Roberto Gandolfi, deceased, late of Gargenville, France, by Isabelle Francoise Gandolfi, Gian-Piero Gandolfi, heirs; Dennis K. Klipa; Neal J. Fetner, both of Midland, Mich.

[73] Assignee: Hoechst Marion Roussel Inc., Cincinnati, Ohio

[21] Appl. No.: 666,715

[22] Filed: Jun. 18, 1996

[30] Foreign Application Priority Data

Jun. 21, 1995 [EP] European Pat. Off. ............ 95401478

[51] Int. Cl.$^6$ ...................................................... C07F 7/08
[52] U.S. Cl. ...................................................... 556/436
[58] Field of Search ............................................. 556/436

[56] References Cited

U.S. PATENT DOCUMENTS

| | | | |
|---|---|---|---|
| 5,523,442 | 6/1996 | Collard et al. | 556/436 X |
| 5,554,780 | 9/1996 | Wolf | 556/436 |
| 5,606,089 | 2/1997 | Tamura et al. | 556/436 |
| 5,679,820 | 10/1997 | Pickett et al. | 556/436 |

FOREIGN PATENT DOCUMENTS

| | | |
|---|---|---|
| 0403713 | 12/1990 | European Pat. Off. |
| 0409676 | 1/1991 | European Pat. Off. |

OTHER PUBLICATIONS deNanteuil, G., Tetrahedron Letters, vol. 32, No. 22, pp. 2467–2468 (1991).

L.S. Chen, et al., J. of Fluorine Chemistry, 18, pp. 117–129 (1981).

G.Chen, et al., J. of Organometallic Chemistry, 251, pp. 149–158 (1983).

K.T. Dishart, et al. J. of the American Chemical Society, vol. 78, pp. 2268–2270 (1956).

A.Sykes, et al., J. of the Chemical Society, pp. 835–839 (1953).

J–M Hornsperger, et al., Biochemical Society Transactions vol. 22, pp. 758–763 (1994).

X.Creary, J. Org. Chem. 52, pp. 5026–5030 (1987).

B. Hassine, et al., Bull. Soc. Chim. Belg. vol. 95/n, pp. 547–556 (1986).

*Primary Examiner*—Paul F. Shaver
*Attorney, Agent, or Firm*—Mark C. Nelligan; Nelsen L. Lentz

[57] ABSTRACT

The present invention relates to a novel process for the preparation of 1-(3-trialkylsilylphenyl)-2,2,2-trifluoromethyl ethanones from 1-halo-3-trialkylsilanyl-benzenes. 1-(3-trialkylsilylphenyl)-2,2,2-trifluoromethyl ethanones are useful for the treatment of Alzheimer's disease and senile dementia. In addition, the present invention relates to a novel process for purifying 1-(3-trialkylsilylphenyl)-2,2,2-trifluoromethyl ethanones utilizing a novel extraction method.

19 Claims, No Drawings

5,760,267

PROCESS FOR PREPARING 1-(3-TRIALKYLSILYLPHENYL)-2,2,2-TRIFLUOROMETHYL ETHANONE DERIVATIVES

BACKGROUND OF THE INVENTION

The present invention relates to a novel process for preparing 1-(3-trialkylsilylphenyl)-2,2,2-trifluoromethyl ethanones which are useful for the treatment of Alzheimer's disease and senile dementia as disclosed by Schirlin, et al. in European Patent Application Publication No. 0 409 676, published Jan. 23, 1991.

SUMMARY OF THE INVENTION

The present invention provides a novel process for the preparation of a compound of the formula (I):

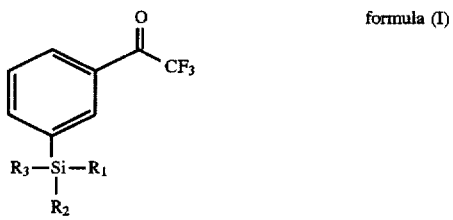

formula (I)

wherein $R_1$, $R_2$ and $R_3$ are each independently $C_1$–$C_4$ alkyl, comprising the steps of;

a) adding one equivalent of a compound of the formula (II):

formula (II)

wherein X is Cl, Br or I; and
$R_1$, $R_2$ and $R_3$ are defined as above, to a mixture of an excess of magnesium in a suitable organic solvent;

b) subsequently adding an excess of lithium trifluoroacetate; and c) subsequently adding a suitable quench solution.

The present invention further provides a novel process for purifying a compound of the formula (I):

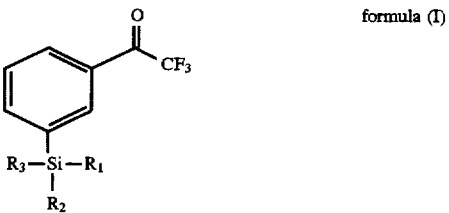

formula (I)

wherein $R_1$, $R_2$ and $R_3$ are each independently $C_1$–$C_4$ alkyl, comprising the steps of;

(a) washing a suitable organic solution of a compound of formula (I), with a methanol/water mixture wherein the methanol/water mixture has a composition by volume of about 50% methanol and 50% water;

(b) extracting the suitable organic solution of step (a) with a methanol/water mixture wherein the methanol/water mixture has a composition by volume of about 80% methanol and 20% water;

(c) concentrating the methanol/water extract of step b to a concentration of about 13% to about 18% by weight of the compound of formula (I);

(d) extracting the concentrated mixture of step c with a suitable organic solvent.

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. As used herein the terms "halo", "halogen" or "halide" refer to a chlorine, bromine or iodine atom. As used herein the term "Pfaudler Reactor" refers to a glass lined steel reactor as appreciated by one of ordinary skill in the art. As used herein the term "baffle" refers to a fixed object placed in the reactor to increase the turbulence and thus improve mixing of the contents within the reactor.

The process for preparing the starting material of formula (II) is described generally in Scheme I. All the substituents, unless otherwise indicated, are previously defined. The reagents and starting materials are readily available to one of ordinary skill in the art.

Scheme I

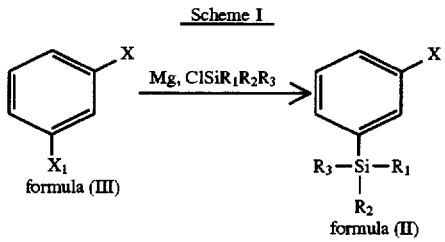

In Scheme I, a compound of formula (II) is prepared from a dihalo compound of formula (III) under the following conditions.

The dihalo compound of formula (III) is combined with magnesium, $ClSiR_1R_2R_3$ and a suitable aromatic solvent under an inert atmosphere, such as nitrogen. It is preferred that all reagents and starting materials be essentially anhydrous. Examples of a dihalo compound of formula (III) are 1,3-dibromobenzene, 1,3-dichlorobenzene, 1-chloro-3-bromobenzene, 1,3-diiodobenzene, 1-chloro-3-iodobenzene and 1-bromo-3-iodobenzene, with the preferred dihalo compound of formula (III) being 1,3-dibromobenzene. The total number of equivalents of magnesium employed in the process of Scheme I relative to the dihalo compound of formula (III) is from about 0.9 eq to about 1.1 eq, with about 1 eq being preferred. In addition, magnesium suitable for Grignard reactions is preferred, such as magnesium powder, magnesium granules, magnesium ribbon, magnesium turnings and the like. Magnesium turnings are most preferred. The reaction vessel is fitted with an agitator, such as a retreat curve agitator. The agitator is set at a speed sufficient for good mixing. The total number of equivalents of $ClSiR_1R_2R_3$ employed in the process of Scheme I relative to the dihalo compound of formula (III) is from about 0.8 eq to about 1.2 eq, with about 1.1 eq being preferred. Examples of $ClSiR_1R_2R_3$ are chlorotriethylsilane, chloro-tri-n-propylsilane, chloro-tri-n-butylsilane, chlorodimethylethylsilane, chlorodimethylisopropylsilane, chlorotrimethylsilane and the like. Chlorotrimethylsilane is the preferred $ClSiR_1R_2R_3$. The mass ratio of suitable aromatic solvent to dihalo compound of formula (III) employed in the process of Scheme I is from about 3 to about 10, with about 4.6 being preferred. For example, as described in Table 1, batch #2, 810 lb of toluene are utilized with 176 lb of 1,3-dibromobenzene resulting in a mass ratio of 4.6 (810 lb/176 lb). Examples of a suitable aromatic solvent are benzene, ethylbenzene, xylene, diethylbenzene, toluene and the like. The preferred suitable aromatic solvent is toluene. The above mixture is heated at a temperature of from about 20° C. to about 80° C. The preferred temperature of the mixture is about 50° C. When the temperature of the mixture begins to fall, the addition of a suitable ether is initiated. Examples of a suitable ether are diethyl ether, tetrahydropyran, tetrahydrofuran, and the like. The preferred suitable ethers are tetrahydropyran and tetrahydrofuran, with tetrahydrofuran being most preferred. The total number of equivalents of suitable ether employed in the process of Scheme I relative to the dihalo compound of formula (III) is from about 1.8 eq to about 4 eq, with about 2.5 eq of suitable ether being preferred. It is preferred that from about 2% to about 15% of the total amount of the suitable ether be added to the mixture in one portion initially, with about 10% of the total amount of the suitable ether being the preferred initial amount added to the mixture. The remaining portion of the total amount of the suitable ether is then added at a rate of from about 0.15 eq/hour to about 2 eq/hour, with about 0.7 eq/hour to about 1.2 eq/hour being preferred and 1.13 eq/hour being the most preferred rate of addition of the suitable ether. The controlled rate of addition of the remaining portion of the total amount of the suitable ether allows the temperature of the reaction to be controlled and essentially maintained at the mixture temperature, such as the preferred temperature of 50° C. It is preferred that the temperature of the process of Scheme I be maintained at about 50° C. during addition of the suitable ether. After addition of the total amount of suitable ether is complete, the reaction is allowed to stir for about 10 hours to about 15 hours at a temperature of from about 20° C. to about 70° C. with about 50° C. being the preferred temperature. The slurry is then cautiously added to water which is at a temperature of from about 5° C. to about 50° C., with stirring. The compound of formula (II) is then isolated and purified by techniques well known in the art, such as extractive methods, distillation, chromatography and the like. For example, the mixture is then stirred for about 10 minutes to about 1 hour. The phases are then separated and the organic phase is optionally subjected to a second water wash. The organic phase is then dried with a suitable drying agent, such as anhydrous magnesium sulfate, filtered and concentrated under vacuum to provide the compound of formula (II) which can be further purified by techniques well known in the art such as chromatography and/or vacuum distillation.

The process of the present invention is described in Scheme II. All the substituents, unless otherwise indicated, are previously defined. The reagents and starting materials are readily available to one of ordinary skill in the art.

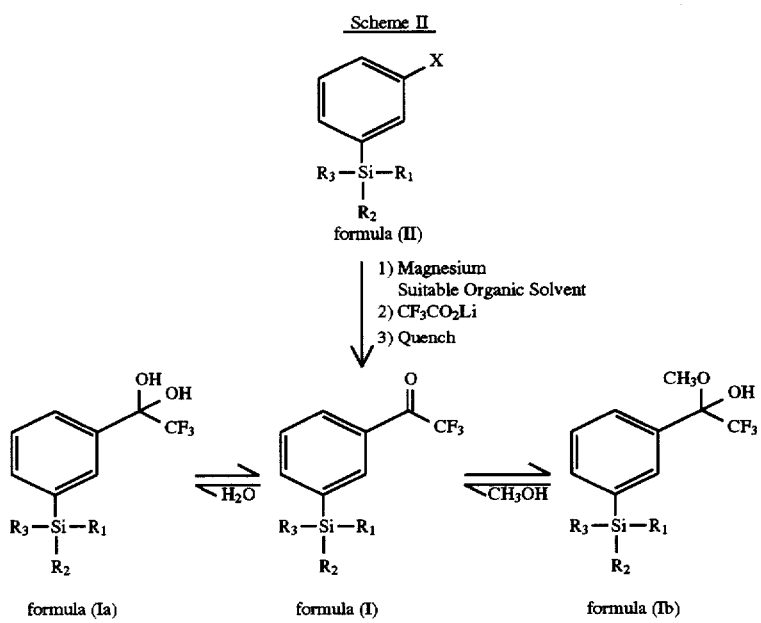

In Scheme II, a suitable reaction vessel, such as a dry 200 gallon Pfaudler reactor, fitted with a retreat curve agitator and a baffle, is charged with an excess of magnesium suitable for Grignard reactions under an inert atmosphere, such as nitrogen. It is preferred that the suitable reaction vessel be charged with 1.0 equivalents of magnesium, with 1.05 equivalents of magnesium being most preferred. Examples of magnesium suitable for Grignard reactions are magnesium powder, magnesium granules, magnesium ribbon, magnesium turnings and the like. Magnesium turnings are preferred. Then about 10 equivalents of a suitable ether are added to the reactor. Examples of a suitable ether are diethyl ether, tetrahydropyran, tetrahydrofuran, and the like. Tetrahydrofuran is the preferred suitable ether. The suitable ether must be essentially anhydrous. It is preferred that the water content of the suitable ether not exceed 100 ppm of water. The mixture is heated at a temperature of about 30° C. to about 55° C., with a preferred temperature of about 45° C. About 0.02 eq to about 0.10 eq of a suitable initiator, such as 1,2-dibromoethane is then added to the mixture. It is preferred that about 0.04 eq of 1,2-dibromoethane be added to the mixture at about 45° C. Initiation occurs when an exotherm is observed subsequent to addition of the suitable initiator. When the temperature steadies at about 45° C., one equivalent of a suitable 1-halo-3-trialkylsilanyl-benzene of formula (II) is added to the reaction vessel. The suitable 1-halo-3-trialkylsilanylbenzene is added slowly until an exotherm is indicated. The suitable 1-halo-3-trialkylsilanyl-benzene is then added at a rate that maintains the temperature of the reaction below about 58° C., preferably below 50° C. Examples of suitable 1-halo-3-trialkylsilanyl-benzenes are 1-bromo-3-trimethylsilanyl-benzene, 1-chloro-3-trimethylsilanyl-benzene, 1-iodo-3-trimethylsilanyl-benzene, 1-bromo-3-triethylsilanyl-benzene, 1-bromo-3-tri-n-propylsilanyl-benzene, 1-bromo-3-dimethylethylsilanyl-benzene, 1-bromo-3-dimethylisopropylsilanyl-benzene, 1-bromo-3-tri-n-butylsilanyl-benzene and the like. The preferred suitable 1-halo-3-trialkylsilanyl-benzene is 1-bromo-3-trimethylsilanyl-benzene. Alternatively, one equivalent of a suitable 1-halo-3-trialkylsilanyl-benzene of formula (II) may be slowly added directly to the magnesium/suitable ether mixture in the reaction vessel with caution, without addition of a suitable initiator. However, extreme caution must be exercised when the suitable initiator is eliminated from the process, as addition of a large amount of the 1-halo-3-trialkylsilanyl-benzene of formula (II) prior to initiation of the exotherm can result in an uncontrollable reaction. After addition of the suitable 1-halo-3-trialkylsilanyl-benzene is complete, the reaction mixture is maintained at a temperature of about 45° C. for about 2 hours to about 4 hours, with about 3 hours being preferred. The reaction mixture is then cooled to about −12° C. to about 0° C., with about 0° C. being preferred. An excess of lithium trifluoroacetate is then added to the reaction mixture at such a rate that the reaction temperature is maintained at less than about 10° C. It is preferred that about 1.3 eq of lithium trifluoroacetate be added to the reaction mixture, with about 1.1 eq being most preferred. In addition, it is preferred that about 1.1 eq of lithium trifluoroacetate be combined with about 10 eq of a suitable organic solvent in a suitable addition reactor, such as a dry 50 gallon glass-lined reactor and agitated at about 90 rpm for about 2–4 hours. Examples of a suitable organic solvent are tetrahydrofuran, diethyl ether, tetrahydropyran, dioxane and the like. The preferred suitable organic solvent is tetrahydrofuran. It is most preferred that about 1.1 eq of lithium trifluoroacetate be combined with the suitable organic solvent. It is preferred that the suitable organic solvent/lithium trifluoroacetate solution be essentially anhydrous prior to addition to the reaction mixture. This can be achieved by drying the suitable ether/lithium trifluoroacetate solution over 3A molecular sieves until the water content of the solution is less than about 200 ppm. The solution is then added to the reaction mixture at such a rate that the reaction temperature is maintained at less than about 10° C. The reaction mixture is then agitated at about 12° C. for about 30 minutes. A suitable quench reactor, such as a 300 gallon Pfaudler reactor fitted with a retreat curve agitator and a baffle is then charged with a suitable quench solution. Examples of suitable quench solutions are aqueous hydrochloric acid, aqueous sulfuric acid, aqueous hydrochloric acid/heptane, water/37% hydrochloric acid/glacial acetic acid/heptane and the like. The preferred suitable quench solution is water/37% hydrochloric acid/glacial acetic acid/heptane. In addition, it is particularly preferred that the water/37% hydrochloric acid/glacial acetic acid/heptane quench solution have a composition by weight of about 73% water, 2% hydrochloric acid (37%), 6% glacial acetic acid and 19% heptane. The suitable quench solution is cooled to less than 5° C. prior to addition of the reaction mixture. The reaction mixture is then added to the suitable quench solution at a rate that maintains the temperature of the quench reactor mixture at less than about 15° C. After the addition is complete, the 200 gallon reactor is rinsed with a suitable organic solvent, such as tetrahydrofuran and the organic rinse is added to the quench reactor. The mixture in the quench reactor is then agitated at about 15° C. for about 15 minutes. Agitation is then stopped and the mixture is allowed to settle for about 40 minutes. The bottom aqueous layer is decanted out of the quench reactor. The upper organic layer is then transferred to a suitable reactor, such as a 200 gallon glass lined reactor which is used as an in-process holding tank.

It is understood by one of ordinary skill in the art that if the starting material of formula (II) used in Scheme II is contaminated with undesired organohalides, such as dihalobenzenes, for example 1,3-dibromobenzene, 1,3-dichlorobenzene, 1-chloro-3-bromobenzene, 1,3-diiodobenzene, 1-chloro-3-iodobenzene and 1-bromo-3-iodobenzene, an additional two equivalents of magnesium in step a and an additional two equivalents of lithium trifluoroactetate in step b must be used in the process of Scheme II for each equivalent of undesired dihalobenzene present in the starting material. For example, if the starting material consists of 1 mole of 1-bromo-3-trimethylsilanyl-benzene contaminated with an additional 0.10 moles of 1,3-dibromobenzene, then under the most preferred conditions 1.25 moles of magnesium must be used in step a and 1.30 moles of lithium trifluoroacetate must be used in step b. The amount of undesired dihalobenzene can be readily determined by techniques and procedures well known in the art, such as gas chromatography.

As with any synthetic process, various undesired by-products are produced along with the desired compound. Thus, it is preferred that the resulting crude material be purified to remove the undesired by-products. For example, the crude product of formula (I) can be purified following the novel extractive procedure set forth in Scheme III. All the substituents, unless otherwise indicated, are previously defined. The materials for extraction are readily available to one of ordinary skill in the art.

Scheme III

Step A
Extraction of the aqueous with a suitable organic solvent, combination with the organic phase and concentration.

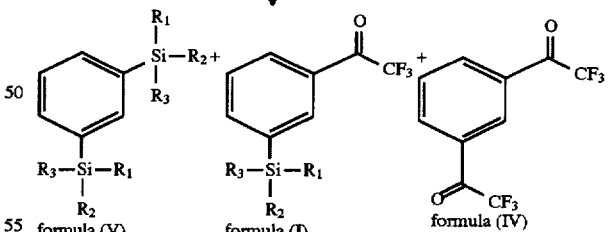

formula (V)  formula (I)  formula (IV)

Step B
Washing of the organic concentrate with methanol/water, 50/50, v/v.

formula (V) + formula (I)

Step C
Extraction of the organic concentrate with with methanol/water, 80/20 v/v.

-continued
Scheme III

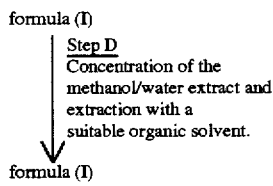

In step A, the decanted aqueous layer obtained in Scheme II, is reloaded into the quench reactor and extracted with a suitable organic solvent. Examples of a suitable organic solvent are heptane, diethyl ether, hexane, toluene, xylene and the like. The preferred suitable organic solvent is heptane. The lower aqueous layer is decanted out of the quench reactor and the upper organic extract is combined with the first organic layer (obtained in scheme II) in the 200 gallon reactor. The combined organic layers are concentrated under vacuum to a concentration of about 30–35% of formula (I) compound by weight in the suitable organic solvent, such as heptane. In step B, the organic solution is washed 2 to 3 times with a methanol/water mixture wherein the methanol water mixture has a composition by volume of about 50% methanol and 50% water, with 3 washes being preferred. This washing step removes undesired by-products of formula (IV). In step C, the organic solution is extracted 3 to 7 times with a methanol/water mixture wherein the methanol/water mixture has a composition by volume of about 80% methanol and 20% water, with 5 extractions being preferred. Step C results in extraction of compounds of formula (I) away from the undesired by-products of formula (V). The methanol/water extracts are then combined and concentrated under vacuum to a concentration of about 13 to 18% of compound of formula (I) in solution (at this concentration two phases result). In step D, the concentrated methanol/water layer is then extracted 1 to 2 times with a suitable organic solvent. Examples of a suitable organic solvent are heptane, diethyl ether, toluene, hexane and the like. Heptane is the preferred suitable organic solvent. A total of 2 extractions are preferred. The organic extracts are then combined and concentrated under vacuum to provide the 1-(3-trialkylsilylphenyl)-2,2,2-trifluoromethyl ethanone derivative of formula (I). The compound of formula (I) exists in equilibrium with the hydrate of formula (Ia) and the hemiacetal of formula (Ib) at various stages of the extraction and purification process described above. The equilibrium can be driven to essentially complete formation of formula (I) by techniques well known in the art, such as molecular sieves, distillation, azeotropic distillation and heating at various pressures. The ratio of the desired compound of formula (I) to the hydrate of formula (Ia) and the hemiacetal of formula (Ib) can be determined by one of ordinary skill in the art, such as by gas chromatography. The compound of formula (I) can be further purified, if necessary, by techniques well known to one of ordinary skill in the art, such as chromatography and/or distillation.

The following examples present typical syntheses as described in Schemes I and II. These examples are understood to be illustrative only and are not intended to limit the scope of the present invention in any way. As used herein, the following terms have the indicated meanings: "ppm" refers to parts per million; "g" refers to grams; "mmol" refers to millimoles; "L" refers to liters; "ml" refers to milliliters; "bp" refers to boiling point; "mp" refers to melting point; "°C." refers to degrees Celsius; "mm Hg" refers to millimeters of mercury; "µL" refers to microliters; "µg" refers to micrograms; "µM" refers to micromolar; "eq" refers to equivalents; "min" refers to minutes; "rpm" refers to revolutions per minute; "THF" refers to tetrahydrofuran; "LiTFA" refers to lithium trifluoroacetate; and "lb" refers to pounds.

EXAMPLE 1

Small scale preparation of 1-bromo-3-trimethylsilanyl-benzene.

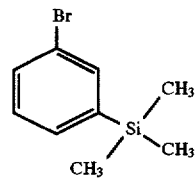

Scheme I; A 500 mL round-bottomed, 3 necked, fluted flask with a thermowell is fitted with an addition funnel, mechanical stirrer, reflux condenser and thermocouple recorder. The atmosphere is flushed with nitrogen. Magnesium (4.84 g, 0.199 mole), chlorotrimethylsilane (45.9 g, 0.422 mole), toluene (214 g) and 1,3-dibromobenzene (46.5 g, 0.197 mole) are then added. The mixture is heated to 50° C. with a heat gun and then allowed to slowly cool. When the temperature starts to fall, tetrahydrofuran (38.1 g) is added. The temperature continues to fall to 42° C. where it stabilizes and then begins to rise. The temperature is controlled at 50°±2° C. while the remaining tetrahydrofuran (342.9 g) is added dropwise (1 drop every 5 to 8 seconds) over a 2 hour period. When about 60–70% of the tetrahydrofuran has been added the exotherm subsides and a fluffy solid forms. The remainder of the tetrahydrofuran is added rapidly without evidence of an exotherm. The mixture is then allowed to cool to room temperature overnight. The slurry is vacuum transferred to a one liter flask containing water heated to 50° C. producing a temperature increase. The mixture is stirred for 10 minutes and the phases are separated (mixture temperature is 45° C. when separated). The organic phase is washed with water (50 mL), dried over anhydrous magnesium sulfate/sodium sulfate, filtered, concentrated under vacuum and distilled through a 40 theoretical plate concentric tube distillation column at 15 mm Hg. The title compound is then collected at a temperature of from 94° C. to 105° C. to provide a colorless oil (32.7 g, 76.8%).

Reverse-phase HPLC (high performance liquid chromatography) analysis of the title compound can be performed utilizing a Hitachi Model L-6200 gradient pump, a Perkin-Elmer Diode Array 235 Detector, a Spectra-Physics Model 4270 integrator, a Hitachi Model AS-2000 autosampler, and a Rheodyne Model 7125 injector equipped with a 20 µL sample loop and a 4.0×80 mm Zorbax ODS (5 µm particles) column. The detector is set at 255 nm, the mobile phase is 90:10 acetonitrile/water and the flow rate is set at 2 mL/min resulting in a retention time (Rt) for the title compound of about 0.92 to 0.95 minutes.

Preparative LC (liquid chromatography) of the title compound can be performed utilizing a Gilson Model 305 pump equipped with a Gilson Manometric Module Model 805, a Linear Model UV-106 (254 nm) detector, a Sargent-Welch Model SRG-2 chart recorder, and a Rheodyne 7125 injector equipped with a 1.0 mL sample loop and an Alltech 22.5× 250 mm Econosphere $C_{18}$ (10 µm particles) column. The crude material is dissolved in acetonitrile prior to injection.

The detector is set at 254 nm, the mobile phase can be 90:10 or 85:15 acetonitrile/water and the flow rate is set at 15 mL/min resulting in an Rt range for the title compound of about 8.5 to 11 minutes.

Gas chromatographic analysis of the title compound can be performed utilizing a Hewlett Packard 5890A Gas Chromatograph, a Hewlett Packard 7573A Autosampler fitted with a 10 µL syringe, a Hewlett Packard 7673 Autosampler Tray, a flame ionization detector, a PE-Nelson AccessChrom Rev. 1.9 with model 941 A/D data system, a Supelco SPB-1 30 m×0.32 mm ID column with 1 µfilm thickness (cut from a 60 m column) and helium as the carrier gas. The conditions used are a 10 psi column head pressure, a 105 mL/min split flow, a 1.8 mL/min column flow, 20 mL/min detector make up (nitrogen), 20 mL/min detector hydrogen flow, 300 mL/min detector air flow, detector range =2, injector temperature of 275° C. and a detector temperature of 300° C. The temperature gradient program used has an initial temperature of 60° C. that increases to 130° C. at a rate of about 16° C./min, it is then held at 130° C. for 12 min, and finally increased to 320° C. at a rate of about 22° C./min at which time the run is terminated. The retention time is approximately 16 min for 1-bromo-3-trimethylsilanyl-benzene.

Example 1a provides the general procedure followed for 10 separate batches for the large scale preparation of 1-bromo-3-trimethylsilanyl-benzene. Following Example 1a, Table 1 provides the individual amounts of reagents and starting materials utilized and the results obtained for each of the 10 batches.

Example 1a

Large scale preparation of 1-Bromo-3-trimethylsilanyl-benzene.

Scheme I, ; Magnesium turnings (18.25 lb) are loaded into a 200 gallon glass-lined reactor fitted with a retreat curve agitator. The reactor is sealed, pressure tested and purged with nitrogen. 1,3-dibromobenzene (176 lb) is then vacuum loaded into the reactor followed by vacuum loading of toluene (806.6 lb). The agitator is set to 130 rpm in order to obtain good mixing. Chlorotrimethylsilane (180 lb) is then loaded into the reactor by adding nitrogen pressure to the cylinder of chlorotrimethylsilane and opening the cylinder to the reactor headspace. After loading the chlorotrimethylsilane, the transfer line is blown clear with nitrogen. The temperature control system of the reactor is set to maintain an internal reactor temperature of 50° C. When the internal temperature and jacket temperature of the reactor stabilize at 50° C., tetrahydrofuran (14 lb) is pumped into the reactor headspace. The temperature of the reactor is monitored to determine when the reaction (exothermic) starts. The reaction is determined to have started when the difference between the internal temperature of the reactor and the jacket temperature is greater than 5°–10° C. After the reaction starts, tetrahydrofuran (130 lb) is pumped into the reactor at a rate of about 0.7 eq/hour to about 1.2 eq/hour. After addition of the tetrahydrofuran is complete, the reactor contents are agitated for an additional 10–15 hours at 50° C.

The contents of the reactor are then transferred to a 300 gallon glass-lined reactor fitted with a pitched blade agitator and containing water (about 100 gallons at 5°–10° C.). Toluene (about 20 lb) is vacuum loaded into the original 200 gallon reactor and is used to flush the transfer line between the 200 gallon and 300 gallon reactors. The 300 gallon reactor is agitated for about one hour, agitation is then stopped and the contents are allowed to settle for about 30–60 minutes. The aqueous phase is then drained out of the 300 gallon reactor and water (about 25 gallons) is again added, followed by agitation for about 30 minutes. The agitation is then stopped, the contents are allowed to settle for about 30–90 minutes and the aqueous layer is drained out of the 300 gallon reactor. The organic phase is then drained to 55 gallon drums.

The 300 gallon reactor is then pressure tested, purged with nitrogen and about 1600–2000 lb of the above organic solution from the 55 gallon drums is vacuum loaded into the reactor. The agitator is set at about 100 rpm and the jacket system set to hold the jacket temperature at 10°–20° C. above the internal temperature to begin distillation of the volatiles into a distillate receiver. As the level in the reactor decreases, additional organic solution from the 55 gallon drums is loaded until 5 batches have been loaded into the reactor. The distillation is continued until the internal temperature of the reactor reaches 68°–72° C. The jacket temperature is then set to about 25° C. and the vacuum is broken with nitrogen. When the internal temperature of the reactor is less then about 35° C., the manway is opened and diatomaceous earth (about 20 lb) and magnesium sulfate (about 20 lb) are loaded into the reactor through the manway. The manway is then closed and the reactor is pressure tested and purged with nitrogen. The contents of the reactor are then drained into 55 gallon drums through a Nutsche filter (prepared by placing a new filter cloth in the bottom) to provide the title compound.

TABLE 1

Summary of Reaction Conditions and % Yield of 1-Bromo-3-trimethylsilanyl-benzene for Ten Individual Batches Following the Procedure Described in Example 1 for each Individual Batch in an Analogous Manner.

| | #1 | #2 | #3 | #4 | #5 | #6 | #7 | #8 | #9 | #10 | total |
|---|---|---|---|---|---|---|---|---|---|---|---|
| Magnesium (lb) | 18.25 | 18.25 | 18.25 | 18.25 | 18.25 | 18.25 | 18.3 | 18.5 | 18.3 | 17.5 | 182 |
| 3-Dibromobenzene (lb) | 176 | 176 | 176 | 176 | 176 | 176 | 176 | 176 | 176.3 | 168.9 | 1753 |
| Toluene (lb) | 806.6 | 810 | 811 | 812 | 810 | 811 | 810 | 810 | 814 | 780 | 8075 |
| Chlorotrimethylsilane (lb) | 176 | 180 | 178 | 159 | 176 | 171 | 172 | 215 | 177 | 138 | 1742 |
| Initial THF (lb) | 28 | 14 | 14 | 14 | 14 | 14 | 14 | 14 | 14.1 | 13.3 | 153 |
| Final THF (lb) | 116 | 130 | 130 | 130 | 130 | 130.1 | 130 | 130 | 120 | 125 | 1271 |
| Total THF (lb) | 144 | 144 | 144 | 144 | 144 | 144.1 | 144 | 144 | 144.1 | 138.3 | 1434.5 |
| Time for final THF addition (min) | 140 | 180 | 140 | 145 | 145 | 135 | 160 | 194 | 210 | 215 | |
| Quench water (gal) | 100 | 100 | 100 | 100 | 100 | 100 | 100 | 100 | 100 | 100 | 1000 |
| Toluene flush (lb) | 21.5 | 20 | 20 | 20 | 20 | 20 | 20 | 28 | 20 | 21 | 211 |
| Water wash (gal) | 25 | 25 | 25 | 25 | 25 | 25 | 25 | 25 | 25 | 25 | 250 |

TABLE 1-continued

Summary of Reaction Conditions and % Yield of 1-Bromo-3-trimethylsilanyl-
benzene for Ten Individual Batches Following the Procedure Described in Example 1 for
each Individual Batch in an Analogous Manner.

| | #1 | #2 | #3 | #4 | #5 | #6 | #7 | #8 | #9 | #10 | total |
|---|---|---|---|---|---|---|---|---|---|---|---|
| Agitator speed (rpm) | 130.4 | 130.8 | 130 | 110 | 110 | 135 | 133 | 135 | 132.5 | 127 | |
| % yield of 1-Bromo-3-trimethylsilanyl-benzene | 64.58 | 68.78 | 63.93 | 64.90 | 63.53 | 64.39 | 64.35 | 63.40 | 66.20 | 66.04 | 65.0 |

EXAMPLE 2

Preparation of 1-Chloro-3-trimethylsilanyl-benzene.

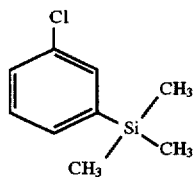

Scheme I; 1-Chloro-3-trimethylsilanyl-benzene is prepared in a manner analogous to the procedure described in examples 1 and 1a utilizing chlorotrimethylsilane and 1-chloro-3-bromobenzene as the dihalo compound of formula (III).

EXAMPLE 3

Preparation of 1-Bromo-3-trimethylsilanyl-benzene.

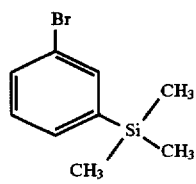

Scheme I; 1-Bromo-3-trimethylsilanyl-benzene is prepared in a manner analogous to the procedure described in examples 1 and 1a utilizing chlorotrimethylsilane and 1-bromo-3-iodobenzene as the dihalo compound of formula (III).

EXAMPLE 4

Preparation of 1-Chloro-3-trimethylsilanyl-benzene.

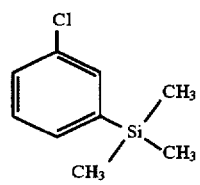

Scheme I; 1-Chloro-3-trimethylsilanyl-benzene is prepared in a manner analogous to the procedure described in examples 1 and 1a utilizing chlorotrimethylsilane and 1-chloro-3-iodobenzene as the dihalo compound of formula (III).

EXAMPLE 5

Preparation of 1-Iodo-3-trimethylsilanyl-benzene.

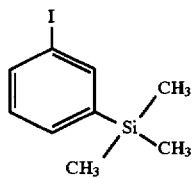

Scheme I; 1-Iodo-3-trimethylsilanyl-benzene is prepared in a manner analogous to the procedure described in examples 1 and 1a utilizing chlorotrimethylsilane and 1,3-diiodobenzene as the dihalo compound of formula (III).

EXAMPLE 6

Preparation of 1-Bromo-3-triethylsilanyl-benzene.

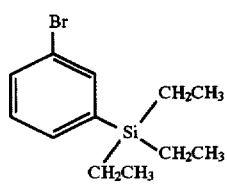

Scheme I; 1-Bromo-3-triethylsilanyl-benzene is prepared in a manner analogous to the procedure described in examples 1 and 1a utilizing 1,3-dibromobenzene and chlorotriethylsilane as the $ClSiR_1R_2R_3$ compound.

EXAMPLE 7

Preparation of 1-Bromo-3-tri-n-propylsilanyl-benzene.

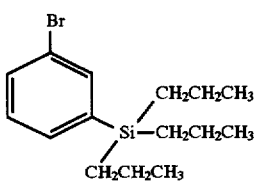

Scheme I; 1-Bromo-3-tri-n-propylsilanyl-benzene is prepared in a manner analogous to the procedure described in examples 1 and 1a utilizing 1,3-dibromobenzene and chloro-tri-n-propylsilane as the $ClSiR_1R_2R_3$ compound.

EXAMPLE 8

Preparation of 1-Bromo-3-dimethylethylsilanyl-benzene.

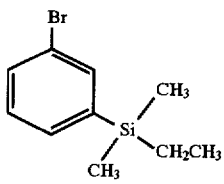

Scheme I; 1-Bromo-3-dimethylethylsilanyl-benzene is prepared in a manner analogous to the procedure described in examples 1 and 1a utilizing 1,3-dibromobenzene and chlorodimethylethylsilane as the $ClSiR_1R_2R_3$ compound.

EXAMPLE 9

Preparation of 1-Bromo-3-dimethylisopropylsilanyl-benzene.

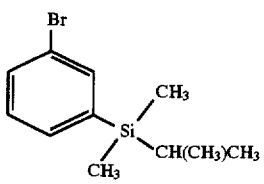

Scheme I; 1-Bromo-3-dimethylisopropylsilanyl-benzene is prepared in a manner analogous to the procedure described in examples 1 and 1a utilizing 1,3-dibromobenzene and chlorodimethylisopropylsilane as the $ClSiR_1R_2R_3$ compound.

EXAMPLE 10

Preparation of 1-Bromo-3-tri-n-butylsilanyl-benzene.

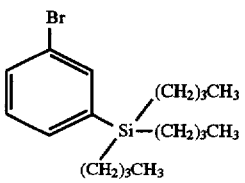

Scheme I; 1-Bromo-3-tri-n-butylsilanyl-benzene is prepared in a manner analogous to the procedure described in examples 1 and 1a utilizing 1,3-dibromobenzene and chloro-tri-n-butylsilane as the $ClSiR_1R_2R_3$ compound.

EXAMPLE 11a

Preparation of 1-(3-trimethylsilylphenyl)-2,2,2-trifluoromethyl ethanone.

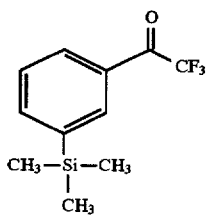

Scheme II; A one liter, three necked round bottom flask fitted with a mechanical stirrer, temperature probe and nitrogen bubbler, is purged with nitrogen. Magnesium turnings (11.9 g, 0.49 mol) and anhydrous tetrahydrofuran (250 g) are added. To this mixture is added 1,2-dibromoethane (2.4 g, 0.0128 mol, DBE) in one shot. An exotherm is detected almost immediately with the temperature rising to 29° C. When the temperature falls to 25° C., 1-bromo-3-trimethylsilanyl-benzene (80.63 g, 0.352 mol, 80.63%) is added over 30 minutes. During the addition, the temperature again rises and is maintained at 50°±2° C. with an ice bath. After the addition is complete, the exotherm subsides and the mixture is then heated at 45° C. with stirring overnight. The temperature of the mixture is then lowered to 0° C. and a solution of lithium trifluoroacetate (352 g, 0.575 mol, 200 ppm water) in tetrahydrofuran (250 g) is added over 30 minutes. The mixture is then allowed to warm to room temperature. It is then vacuum transferred to a stirred mixture of water (583 g), glacial acetic acid (51 g), aqueous hydrochloric acid (27 g, 37%) and heptane (142 g) while maintaining the temperature at approximately 10°–15° C. After addition is complete, the mixture is allowed to warm to 20° C. The layers are then separated and the aqueous layer is extracted with heptane (50 g). The organic layer and organic extract are combined and concentrated under vacuum (45° C., 45 mmHg) to a concentration of 38.5%. This solution is then washed with methanol/water (50/50, v/v, 4×185 g). The solution is then extracted with methanol/water (80/20, v/v, 5×185 g). The combined extracts are partially concentrated under vacuum (45° C., 45 mmHg). The two phase mixture is then extracted with heptane (150 g). The organic extract is then dried over anhydrous magnesium sulfate, filtered and concentrated under vacuum (45° C., 45 mmHg) to provide the title compound as a light yellow oil (78.2 g, 77.5% overall yield). The title compound can be further purified by distillation through a 40 theoretical plate concentric tube distillation column (94°–105° C., 15 mmHg) to provide the title compound as a colorless oil.

Example 11b provides the general procedure followed for 10 separate batches for the large scale preparation of 1-(3-trimethylsilylphenyl)-2,2,2-trifluoromethyl ethanone. Following example 11b, Table 2 provides a summary of reaction conditions and % Yield of 1-(3-trimethylsilylphenyl)-2,2,2-trifluoromethyl ethanone for 10 individual batches following the procedure described in example 11b for each individual batch in an analogous manner.

EXAMPLE 11b

Scale-up procedure for the preparation of 1-(3-trimethylsilylphenyl)-2,2,2-trifluoromethyl ethanone.

Scheme II; A 200 gallon glass-lined Pfaudler reactor fitted with a retreat curve agitator and a baffle (designated reactor A), and a 50 gallon glass-lined reactor (designated reactor B) are dried at 80° C. while pulling a vacuum and sweeping the reactors with nitrogen. Magnesium turnings (15.2 lb) are loaded into reactor A through the manway, followed by addition of tetrahydrofuran (390 lb). The tetrahydrofuran is first sampled and analyzed for water content, with an upper limit of 100 ppm of water in the tetrahydrofuran being permitted. The agitator in reactor A is set to 100 rpm. The reactor A jacket is set for master/slave control with an internal temperature setpoint of 45° C. When the reactor A internal temperature steadies at about 45° C., about 2.8 to 3.6 lb of 1,2-dibromoethane are loaded into reactor A. The load line is flushed with 3 lb of tetrahydrofuran and the jacket temperature is monitored for the exotherm indicating reaction initiation. When the reaction initiates and the internal temperature of reactor A steadies at about 45° C., 1-bromo-3-trimethylsilanyl-benzene (6 to 8 lbs) is loaded into reactor A. A nitrogen operated Teflon diaphragm pump is used to control the addition of 1-bromo-3-trimethylsilanyl-benzene to the reaction vessel. The jacket temperature is monitored for the exotherm indicating reaction initiation. When the reaction initiates, the remaining 1-bromo-3-trimethylsilanyl-benzene (120–122 lb) are loaded into reactor A maintaining the internal temperature at less than about 50° C. After addition is complete, the load line is flushed with tetrahydrofuran (5 lb). The mixture is then maintained at a temperature of about 45° C. for approximately 3 hours. The mixture is then cooled to about 0° C. Lithium trifluoroacetate (about 88 lbs, LiTFA) and tetrahydrofuran (about 300 lb) are loaded into reactor B and agitated at 90 rpm for about 2–4 hours. The lithium trifluoroacetate/tetrahydrofuran solution is then transferred to reactor A while maintaining the internal temperature in reactor A at less than about 10° C. The transfer is stopped as needed to maintain the reactor A internal temperature at less than about 10° C. After addition is complete, tetrahydrofuran (about 64 lb) is loaded into reactor B. This tetrahydrofuran rinse is then transferred to reactor A and the mixture is agitated at about 12° C. for about 30 minutes. A 300 gallon glass-lined Pfaudler reactor (designated reactor C) fitted with a retreat curve agitator and a baffle is charged with a quench solution consisting of water (about 751 lb), 37% aqueous hydrochloric acid (about 22 lb), glacial acetic acid (65 lb) and heptane (190 lb). The quench solution is cooled to less than 5° C. and the reaction mixture in reactor A is transferred to reactor C, maintaining the internal temperature of reactor C at less than about 15° C. After addition is complete, tetrahydrofuran (about 60 lb) is added to reactor A which is then transferred to reactor C. The mixture in reactor C is then agitated at about 15° C. for at least 15 minutes. Agitation is then stopped and the solution is allowed to settle for at least 40 minutes. The bottom aqueous layer is decanted to drums. The upper organic layer is transferred to a 200 gallon glass lined reactor (designated reactor D) which is used as a distillate receiver and an in-process hold tank. The earlier removed aqueous layer is reloaded into reactor C and is extracted with heptane (100 lb). The lower aqueous layer is drained to drums, and the upper organic layer is transferred to reactor D and combined with the first organic layer. The combined organic layers are concentrated at a vacuum at the pump inlet of about 25 mmHg with an internal temperature of 25°–30° C. and a jacket temperature of about 40°–45° C. The solution is concentrated to about 40 gallons. This concentrated solution is then transferred to reactor B and concentrated further to about 30–35% title compound by weight in heptane. Additional heptane is loaded as needed to achieve the desired weight percent of title compound in heptane. This organic solution is then washed three times with a mixture of methanol/water (50/50, v/v, 180 lb). The organic solution is then extracted five times with a mixture of methanol/water (80/20, v/v, 190 lb). The methanol/water extracts are combined and concentrated under vacuum of about 25 mmHg and an internal temperature of about 20°–25° C. to about 13 to 18% of title compound in solution at which point two phases result. The concentrated methanol/water layer is extracted twice with heptane (250 lb). The combined heptane extracts are then concentrated under vacuum to provide the title compound.

The title compound can be further purified through distillation. For example, the title compound isolated above (436 lb) is vacuum loaded into a 100 gallon glass-lined reactor which is the distillation vessel and reboiler. A 4 inch distillation column containing 4 feet of structure packing is connected to the head space of the distillation vessel and is equipped with a reflux splitter for either distillate reflux or collection. A 28 ft$^2$ Hastalloy C tube heat exchanger is used as the condenser. A 50 gallon glass lined reactor is used as the distillate receiver. The distillation vessel agitator is set to about 80 rpm. The jacket temperature of the distillation vessel is set to 150° C. with a maximum temperature difference of 30° C. between the jacket and internal temperatures. The lights fraction is collected at about 150–200 mmHg until the internal temperature of the distillation vessel reaches 140° C. The contents of the distillate receiver are then drained and the temperature of the distillation vessel is dropped to less than 50° C. The pressure is lowered to about 15 mmHg. The jacket temperature of the distillation vessel is set to 150° C. with a maximum temperature difference of 30° C. between the jacket and internal temperatures. With the reflux splitter set to a reflux ratio of from 3:1 to 10:1, the low boiling impurities are distilled off until the overhead temperature levels off at about 100° to 105° C. The distillate receiver is then drained. The reflux ratio is then set to 1:1 or less and the title compound is distilled off until no additional material will distill over. The product fraction in the distillate receiver is then transferred to a shipping drum through a 0.1 micron polish filter to provide the further purified title compound. If necessary, this material can be re-distilled under conditions analogous to those described above, by one of ordinary skill in the art.

TABLE 2

| Batch No./wgt (lb) | #1 | #2 | #3 | #4 | #5 | #6 | #7 | #8 | #9 | #10 |
|---|---|---|---|---|---|---|---|---|---|---|
| Magnesium | 15.3 | 15.2 | 15.2 | 15.2 | 15.2 | 15.2 | 15.2 | 15.2 | 15.2 | 15.2 |
| Tetrahydrofuran | 399 | 398 | 398 | 398 | 398 | 398 | 398 | 399 | 398 | 400 |
| 1,2-Dibromoethane | 3.1 | 3.5 | 3.2 | 3.4 | 3 | 3.6 | 2.8 | 3.5 | 3.1 | 3.5 |
| 1-Bromo-3-trimethylsilanyl-benzene | 128 | 128.2 | 128.0 | 128.0 | 128.0 | 128.0 | 128.0 | 128.0 | 128.5 | 128.0 |
| LiTFA | 88.7 | 88.6 | 87.8 | 88.0 | 88.0 | 88.0 | 88.0 | 88.0 | 88.0 | 87.0 |
| THF combined with LiTFA | 300 | 301 | 300 | 300 | 300 | 301 | 344 | 300 | 300 | 300 |
| LiTFA/THF addition (min) | 60 | 60 | 59 | 44 | 60 | 60 | 65 | 60 | 55 | 60 |
| THF Rinse of Reactor B | 64 | 64 | 64 | 64 | 64 | 64 | 64 | 65 | 65 | 66 |
| Quench water | 909 | 751 | 751 | 751 | 751 | 751 | 751 | 751 | 751 | 751 |
| 37% HCl | 22 | 22 | 22 | 22 | 22 | 22 | 22 | 22 | 22 | 22 |
| Glacial Acetic Acid | 63 | 65 | 65 | 65 | 65 | 65 | 65 | 65 | 65 | 65 |
| Heptane | 191 | 190 | 190 | 190 | 190 | 190 | 190 | 190 | 191 | 196 |
| Quench Addition (min) | 210 | 25 | 25 | 25 | 20 | 20 | 25 | 12 | 10 | 20 |
| THF rinse of Reactor A | 60 | 60 | 60 | 60 | 60 | 60 | 60 | 60 | 60 | 60 |
| Title Compound (wgt) | 70.9 | 76.9 | 77.7 | 75.1 | 82.7 | 73.3 | 69.7 | 80.8 | 77.4 | 82.1 |
| Percent Yield | 66.5 | 72.0 | 72.9 | 70.4 | 77.6 | 68.7 | 65.3 | 75.8 | 72.3 | 77.1 |

Gas chromatographic analysis of the final isolated title compound can be performed utilizing a Hewlett Packard 5890A Gas Chromatograph, a Hewlett Packard 7573A Autosampler fitted with a 10 µL syringe, a Hewlett Packard 7673A Autosampler Tray, a flame ionization detector, a Nelson AccessChrom data system, a Supelco SPB-1 30 m×0.32 mm ID column with 1 µfilm thickness and helium as the carrier gas. The conditions used are a 10 psi column head pressure, a 105 mL/min split flow, a 1.8 mL/min column flow, 20 mL/min detector make up (nitrogen), 20 mL/min detector hydrogen flow, 300 mL/min detector air flow, injector temperature of 275° C. and a detector temperature of 300° C. The temperature gradient program used has an initial temperature of 120° C. which is held for 22 minutes and then increases to a final temperature of 320° C. at a rate of about 30° C./min at which time the run is terminated.

TABLE 3

Approximate Retention Times Using the Above Analytical Method.

| Compound | Retention Time (min) |
| --- | --- |
| trifluoroacetophenone | 3.1 |
| 2-chloro-p-xylene | 6.0 |
| 1-(3-trimethylsilylphenyl)-2,2,2-trifluoromethyl ethanone | 10.0 |
| 1-(3-trimethylsilylphenyl)-2,2,2-trifluoromethyl ethanone hemiacetal | 20.5 |
| 1-(3-trimethylsilylphenyl)-2,2,2-trifluoromethyl ethanone hydrate | 21.7 |

What is claimed is:

1. A process for the preparation of a compound of the formula (I):

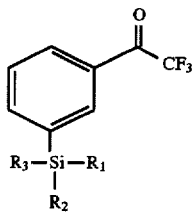

formula (I)

wherein $R_1$, $R_2$ and $R_3$ are each independently $C_1$–$C_4$ alkyl, comprising the steps of;

(a) adding one equivalent of a compound of the formula (II):

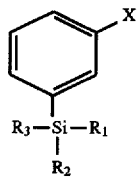

formula (II)

wherein X is Cl, Br or I; and $R_1$, $R_2$ and $R_3$ are defined as above, to a mixture of an excess of magnesium in a suitable organic solvent;

(b) subsequently adding an excess of lithium trifluoroacetate; and (c) subsequently adding a suitable quench solution.

2. A process according to claim 1, further comprising, addition of a suitable initiator to the mixture of the excess of magnesium in the suitable organic solvent prior to addition of the compound of formula (II) in step (a).

3. A process according to claim 2 wherein the suitable initiator is 1,2-dibromoethane.

4. A process according to claim 3 wherein $R_1$, $R_2$ and $R_3$ are each methyl.

5. A process according to claim 4 wherein X is Br.

6. A process according to claim 5 wherein the suitable organic solvent in step (a) is tetrahydrofuran.

7. A process according to claim 6 wherein 1.05 equivalents of magnesium are combined with the tetrahydrofuran in step (a).

8. A process according to claim 7 wherein 1.1 equivalents of lithium trifluoroacetate are added in step (b).

9. A process according to claim 8 wherein the lithium trifluoroacetate is combined with tetrahydrofuran prior to addition in step (b).

10. A process according to claim 9 wherein the lithium trifluoroacetate/tetrahydrofuran solution has a water content of less than about 200 ppm.

11. A process according to claim 10 wherein the suitable quench solution comprises water/37% hydrochloric acid/ glacial acetic acid/heptane.

12. A process according to claim 11 wherein the suitable quench solution has a composition by weight of about 73% water, 2% hydrochloric acid (37%), 6% glacial acetic acid and 19% heptane.

13. A process for purifying a compound of the formula (I)

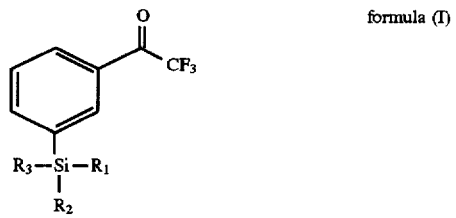

formula (I)

wherein $R_1$, $R_2$ and $R_3$ are each independently $C_1$–$C_4$ alkyl, comprising the steps of;

(a) washing a suitable organic solution of a compound of formula (I), with a methanol/water mixture wherein the methanol/water mixture has a composition by volume of about 50% methanol and 50% water:

(b) extracting the suitable organic solution of step (a) with a methanol/water mixture wherein the methanol/water mixture has a composition by volume of about 80% methanol and 20% water:

(c) concentrating the methanol/water extract of step b to a concentration of about 13% to about 18% by weight of the compound of formula (I);

(d) extracting the concentrated mixture of step c with a suitable organic solvent.

14. A process according to claim 13 wherein the extract of step (d) is concentrated.

15. A process according to either claim 13 or claim 14 wherein the compound of formula (I) is produced by a process comprising the steps of:

(a) adding one equivalent of a compound of the formula

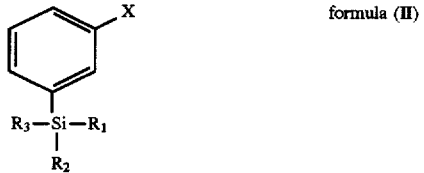

formula (II)

wherein X is Cl, Br or I; and $R_1$, $R_2$ and $R_3$ are defined as above, to a mixture of an excess of magnesium in a suitable organic solvent;

(b) subsequently adding an excess of lithium trifluoroacetate; and (c) subsequently adding a suitable quench solution.

16. A process according to claim 15 wherein $R_1$, $R_2$ and $R_3$ are methyl and X is Br.

17. A process according to claim 16 wherein the suitable organic solution of a compound of formula (I) in step (a) is a heptane solution of a compound of formula (I).

18. A process according to claim 17 wherein the heptane solution of the compound of formula (I) has a concentration of 30% to 35% by weight of the compound of formula (I) in the heptane.

19. A process according to claim 18 wherein the suitable organic solvent in step (d) is heptane.

* * * * *